US009750534B2

(12) United States Patent
Philippon et al.

(10) Patent No.: US 9,750,534 B2
(45) Date of Patent: Sep. 5, 2017

(54) DEVICE AND METHOD FOR HIP DISTENTION AND ACCESS

(71) Applicant: HIPCO, Inc., Vail, CO (US)

(72) Inventors: Marc Joseph Philippon, Vail, CO (US); David Leo Bombard, Edwards, CO (US); John Michael Egan, Hollywood, FL (US)

(73) Assignee: HIPCO, INC., Vail, CO (US)

( * ) Notice: Subject to any disclaimer, the term of this patent is extended or adjusted under 35 U.S.C. 154(b) by 0 days.

(21) Appl. No.: 14/482,388

(22) Filed: Sep. 10, 2014

(65) Prior Publication Data

US 2014/0378982 A1 Dec. 25, 2014

Related U.S. Application Data

(63) Continuation of application No. 12/259,907, filed on Oct. 28, 2008, now Pat. No. 8,858,563.

(Continued)

(51) Int. Cl.
*A61B 17/56* (2006.01)
*A61B 17/02* (2006.01)
(Continued)

(52) U.S. Cl.
CPC ............ *A61B 17/56* (2013.01); *A61B 17/025* (2013.01); *A61B 17/0401* (2013.01); *A61B 17/32* (2013.01);
(Continued)

(58) Field of Classification Search
CPC ................... A61B 17/025; A61B 17/05; A61B 2017/0268; A61B 2017/02756
See application file for complete search history.

(56) References Cited

U.S. PATENT DOCUMENTS 5,163,949 A 11/1992 Bonutti
5,188,630 A 2/1993 Christoudias
(Continued)

FOREIGN PATENT DOCUMENTS

KR 2007094374 10/2009
KR 20090112214 10/2009
(Continued)

OTHER PUBLICATIONS

English Patent Abstract of WO/2007/094374 A1 from espacenet, published Aug. 23, 2007 (1 page).
(Continued)

*Primary Examiner* — Howie Matthews
(74) *Attorney, Agent, or Firm* — Burns & Levinson LLP; Joseph M. Maraia

(57) ABSTRACT

A device for accessing and distending a joint comprises a distraction structure having a generally tapered distal portion adapted to penetrate a tissue region and create an access space within a joint. The distraction structure also includes a lumen extending from a proximal surface to a distal portion. The device further includes a distention structure deployable through the lumen and adapted to exert a force between a first joint surface and a second joint surface and create a working space. The distention structure may, in some embodiments, include an elongate member having a proximal end, a distal end, and a lumen extending along at least a portion of the length of the elongate member, a first expandable region deployable from a first substantially collapsed position to a second substantially expanded position, the first expandable region adapted to exert a force between the first joint surface from the second joint surface.

16 Claims, 14 Drawing Sheets

Related U.S. Application Data

(60) Provisional application No. 60/983,877, filed on Oct. 30, 2007, provisional application No. 60/989,874, filed on Nov. 23, 2007.

(51) Int. Cl.
  *A61B 17/04* (2006.01)
  *A61B 17/32* (2006.01)
  *A61B 17/34* (2006.01)
  *A61B 17/00* (2006.01)
  *A61B 17/29* (2006.01)

(52) U.S. Cl.
  CPC ... *A61B 17/3415* (2013.01); *A61B 2017/0046* (2013.01); *A61B 2017/00473* (2013.01); *A61B 2017/00557* (2013.01); *A61B 2017/00849* (2013.01); *A61B 2017/0268* (2013.01); *A61B 2017/0275* (2013.01); *A61B 2017/2925* (2013.01); *A61B 2017/320044* (2013.01); *A61B 2017/3445* (2013.01)

(56) References Cited

U.S. PATENT DOCUMENTS

| | | | |
|---|---|---|---|
| 5,342,386 A | 8/1994 | Trotta | |
| 5,454,365 A | 10/1995 | Bonutti | |
| 5,827,318 A | 10/1998 | Bonutti | |
| 6,468,289 B1 | 10/2002 | Bonutti | |
| 6,482,209 B1 | 11/2002 | Engh et al. | |
| 6,620,181 B1 | 9/2003 | Bonutti | |
| 6,859,661 B2 | 2/2005 | Tuke | |
| 6,860,892 B1 | 3/2005 | Tanaka et al. | |
| 7,217,273 B2 | 5/2007 | Bonutti | |
| 8,206,447 B2 | 6/2012 | de Villiers et al. | |
| 2001/0001315 A1 | 5/2001 | Bates et al. | |
| 2003/0004460 A1 | 1/2003 | Bedell | |
| 2003/0032963 A1 | 2/2003 | Reiss et al. | |
| 2003/0114878 A1 | 6/2003 | Diederich et al. | |
| 2005/0124843 A1 | 6/2005 | Singh | |
| 2005/0267482 A1 | 12/2005 | Hyde | |
| 2006/0015171 A1 | 1/2006 | Armstrong | |
| 2006/0149136 A1 | 7/2006 | Seto et al. | |
| 2006/0293685 A1 | 12/2006 | Stone et al. | |
| 2007/0173946 A1 | 7/2007 | Bonutti | |
| 2007/0260178 A1 | 11/2007 | Skerven et al. | |
| 2008/0051627 A1 | 2/2008 | Raju | |
| 2008/0086073 A1 | 4/2008 | McDaniel | |
| 2009/0048623 A1 | 2/2009 | Lafosse et al. | |
| 2010/0010303 A1 | 1/2010 | Bakos | |
| 2010/0100114 A1 | 4/2010 | Berger | |
| 2010/0217086 A1 | 8/2010 | Deshmukh et al. | |

FOREIGN PATENT DOCUMENTS

| | | |
|---|---|---|
| WO | 9222259 | 12/1992 |
| WO | 0023009 | 4/2000 |

OTHER PUBLICATIONS

ISA/US, Blain R. Copenhaver, "PCT International Search Report Dated Jan. 21, 2009", Jan. 21, 2009, Publisher: PCT, Published in:US.

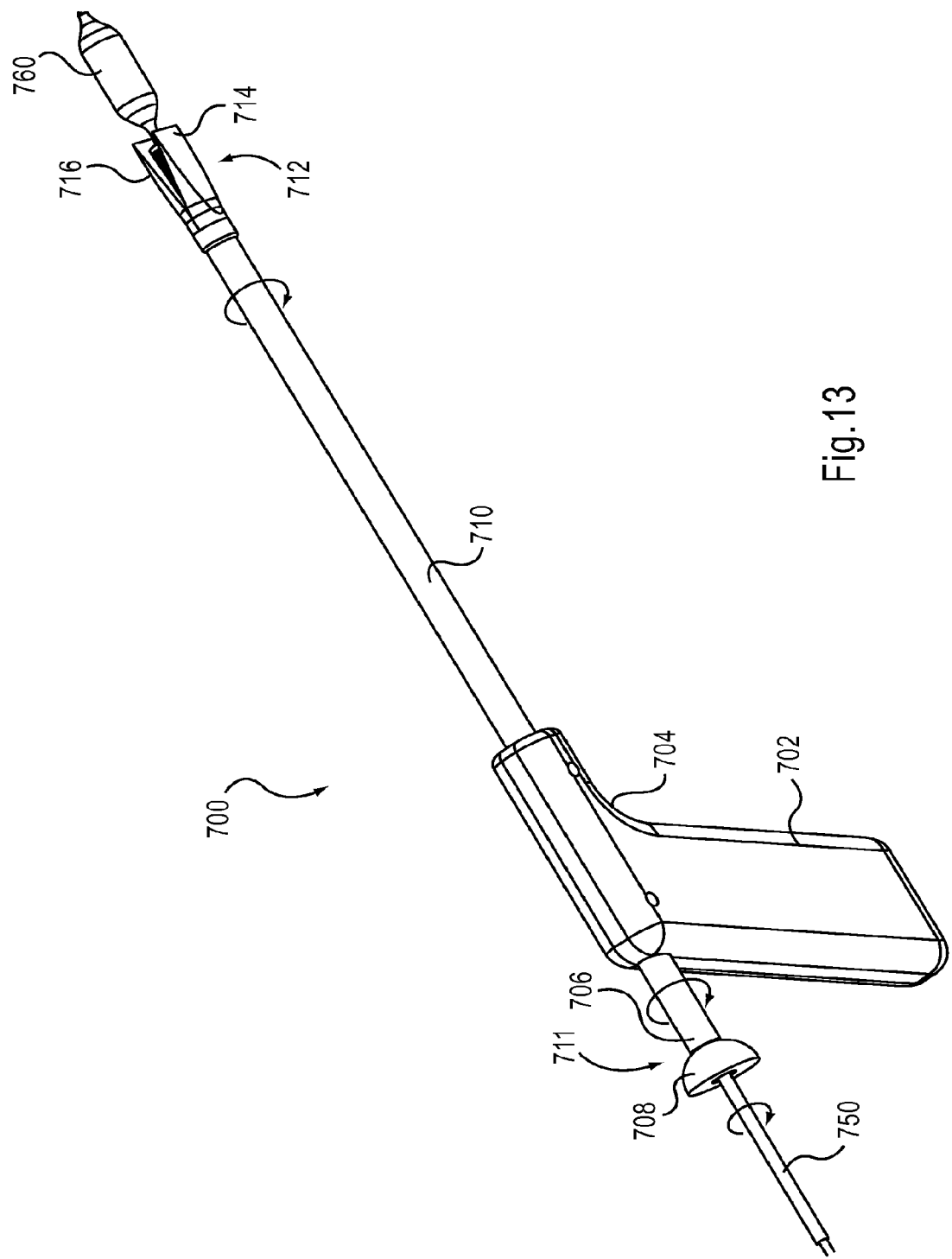

US 9,750,534 B2

DEVICE AND METHOD FOR HIP DISTENTION AND ACCESS

PRIORITY AND CROSS REFERENCE TO RELATED APPLICATIONS

This application is a continuation of prior U.S. application Ser. No. 12/259,907, filed Oct. 28, 2008, now U.S. Pat. No. 8,858,563 claims the benefit of Provisional U.S. Patent Application No. 60/983,877 filed on Oct. 30, 2007 and Provisional U.S. Patent Application No. 60/989,874 filed on Nov. 23, 2007. The details of these Application Nos. 12/259,907 and 60/983,877 and 60/989,874 are incorporated by reference into the present application in their entirety and for all proper purposes.

FIELD OF THE INVENTION

Aspects of the present invention relate to devices and methods for the atraumatic distention of the head of the femur away from the acetabulum in order to create a working space for a variety of endoscopic hip surgeries. Other aspects relate to devices and methods for distending soft tissue structures from the neck of the femur. More particularly, aspects of the present invention pertain to devices and methods that utilize balloons, or other atraumatic means and/or devices, to distend the head of the femur away from the acetabulum in order to create a working space for a variety of endoscopic hip surgeries

BACKGROUND AND DESCRIPTION

Endoscopic hip surgeries such as joint arthroscopy, debridement, joint flushing and joint smoothing are relatively common procedures for the general treatment of hip pathology that leads to painful joints. An important step in these procedures is to assure that the joint surfaces are properly accessible by the surgeon and that good visualization is provided. Current methods for accessing the joint surfaces involve the use of a mechanical rack and pinion system that attaches to the foot of the patient to mechanically pull the femur away from the acetabulum (traction). This type of manual dislocation of the femoral head from the socket is extremely traumatic and invasive to both the patient and the surgical room staff that is tasked with maneuvering the patient's leg. This method of distention is also only marginally effective and the possible side effects to the surgery include numbness, nerve damage, impotence, deep vein thrombosis and pulmonary embolus associated with damage to the veins. Additionally, the leg in traction is not easily manipulated to allow visualization of the articular cartilage areas. Therefore, a less traumatic and less damaging method is needed to create a working space between the femur and acetabulum in order to perform one of a variety of hip procedures. Additionally, because soft tissue structures located within the hip joint contribute to the difficulty of working in this area, a device is needed to manage or otherwise move these tissue structures from the hip capsule.

SUMMARY OF THE INVENTION

In accordance with one aspect, a device for distending a first body tissue from a second body tissue comprises a flexible elongate member, the flexible elongate member including first and second lumens extending at least a portion of the length of the elongate member, a first distention member coupled to the first lumen and deployable from a substantially collapsed position to a substantially expanded position, and a second distention member coupled to the second lumen and deployable from a substantially collapsed position to a substantially expanded position.

In accordance with another aspect, a device for accessing and distending a joint comprises a distraction structure having a generally tapered distal portion adapted to penetrate a tissue region and create an access space within a joint. The device includes a lumen extending from a proximal surface to a distal portion, a distention structure deployable through the lumen and adapted to exert a force between a first joint surface and a second joint surface and create a working space.

In accordance with another aspect, a method of accessing a space within a joint including at least a partial seal formed by one or more tissue structures comprises accessing the joint between a first joint surface and a second joint surface to create a first working space, inserting a distraction device into the first working space, using the distraction device to break the partial seal formed by the one or more tissue structures, at least partially internally distracting the first joint surface from the second joint surface, advancing the distraction device to a first location within the joint, advancing a first distention device proximate to the first location, using the distention device to distend the first joint surface from the second joint surface at a point proximate the first location to create a second working space, and performing a surgical procedure proximate the second working space.

Various other aspects will become apparent as disclosed herein and as would be known to those of skill in the art.

BRIEF DESCRIPTION OF THE DRAWINGS

Various objects and advantages and a more complete understanding of the present invention are apparent and more readily appreciated by reference to the following Detailed Description and to the appended claims when taken in conjunction with the accompanying Drawings, wherein:

FIG. 13 is one embodiment of a surgical tool constructed in accordance with aspects of the present invention;

DETAILED DESCRIPTION

Figure 1:
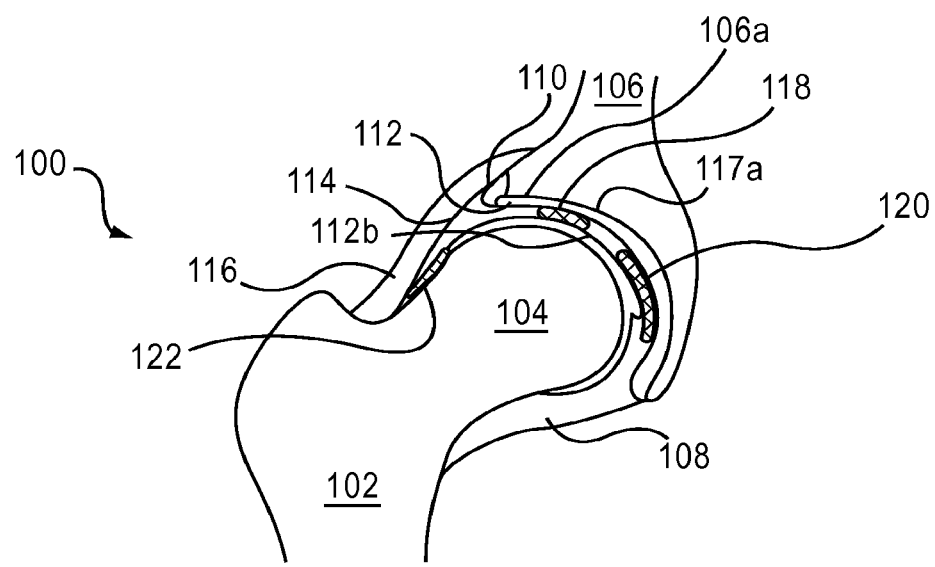
FIG. 1 is a cross section of a human hip joint showing details of where the femoral head engages with the socket of the hip

With reference to FIG. 1, a generalized cross section of a human hip joint 100 is shown. For simplicity, only the major regions of the hip anatomy are indicated in FIG. 1 so that aspects of a device constructed in accordance with the present invention may be described. Shown in FIG. 1 are the femur 102 and the femoral head 104. In a healthy anatomy, the femoral head 104 engages snugly with the acetabulum 106, and more particularly with the inner concave surface 106a of the acetabulum. Where the head of the femur 104 meets the acetabulum 106 is referred to generally as the hip joint. For many endoscopic hip surgeries, the region where the femoral head engages with the acetabulum is the area where most operative procedures take place and where reconstructive or repair techniques are applied to the patient. It is therefore important to gain good access and visualization to this region, and in particular the joint surfaces, during a surgical procedure.

In accordance with one general aspect of the present invention, a series of inflatable or expandable distention structures are placed between the femoral head 104 and the concave portion 106a of the acetabulum 106. As shown in FIG. 1, these structures are referred to as reference numbers 118, 120, and 122 and are shown in their un-expanded or deflated positions. Both the femoral head 104 and the concave surface 106a of the acetabulum 106 include articular cartilage 112 that aids in allowing the hip joint to move freely and pain free. The overall anatomy of the hip joint 100 also includes ligaments and joint capsules 108 and 114 as well as a synovial membrane 116. Acetabular labrum 110 is a ring of cartilage that surrounds the acetabulum and functions to deepen the acetabulum, making it more difficult for the head of the femur 104 to slip out of place. Aspects of the present invention provide access for surgical techniques such as repair and/or reconstruction of the acetabular labrum.

Figure 2:
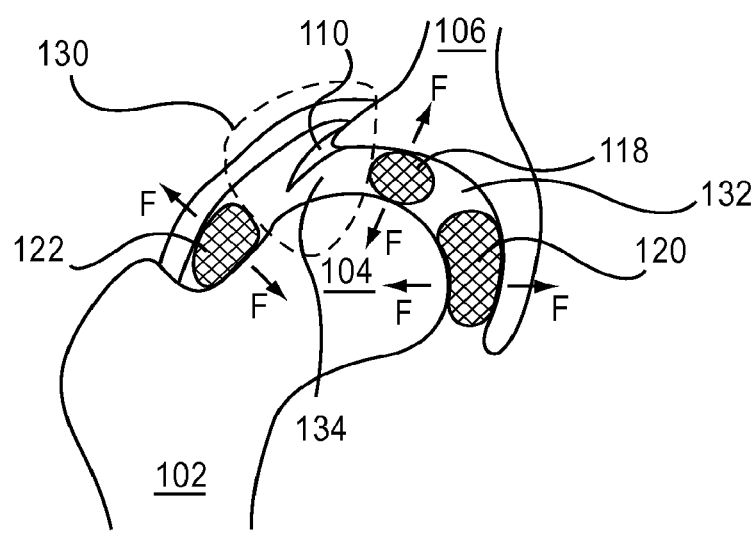
FIG. 2 is a further embodiment of FIG. 1.

While various inflatable devices and techniques are known to gain access to the region between the femoral head 104 and the acetabular surface 106a, none have addressed the particular surgical access problems that exist in hip joint anatomy. FIG. 2 illustrates the general aspects of the inflatable and/or expandable distention structures 118, 120, and 122 in their expanded and/or inflated position, showing the region or zone of work 130 created proximate the acetabular labrum 110, and the general working space 132 and 134 created between the acetabular surface 106a and the femoral head 104.

Various embodiments of the distention structures 118, 120, and 122 and various embodiments of devices that provide access to and delivery of the structures 118, 120, and 122 are described in further detail below.

With continuing reference to FIG. 2, the distention structures 118, 120, and 122 are shown in their expanded and/or inflated positions and, as such, are exerting a force F between the acetabular surface 106a and the femoral head 104. This force thus distends the acetabular surface 106a away from the femoral head 104 creating zone of work 130 and potentially additional working spaces 132 and 134, depending on the number and size of distention structures being used. Zone of work 130 and working space 134 is sometimes referred to as the Peripheral Compartment. It is the space in the joint capsule around the neck and head of the femur that can be accessed with the head of the femur in the acetabulum. This area may extend all the way around to the inferior part of the femur. Working space 134 is sometimes referred to as the Central Compartment and represents the virtual space that exists when the femoral head is moved away from the acetabulum. Depending on the surgical procedure being employed, the particular pathology of the hip joint being addressed by the surgery, and the specific access needs of the surgeon during the procedure, various numbers, sizes, and shapes of distention structures 118, 120, and 122 may be employed.

As will become apparent throughout this description, the number, size and shape of the distention structures will vary greatly depending on the particular application. By showing three such distention structures in FIGS. 1 and 2, or by showing any particular number and/or size of distention structures in connection with other figures or embodiments, there is no intention to limit the scope of the invention to these particular embodiments. In contrast, it is envisioned that a wide range of sizes, shapes, materials, and configurations of distention structures, along with various applicators or other delivery devices are contemplated herein. Because the surface of the femoral head 104 and the acetabular surface 106a, are complex geometries, and the pathology of the particular patient might involve any portion of these surfaces or regions, it is important that a surgeon have at his disposal a wide variety of mechanisms to gain proper access and visualization to these areas. Among other aspects, it is these problems that the prior art fails to adequately address.

Turning to FIGS. 3A-3F, various embodiments of distention structures constructed in accordance with aspects of the present invention are shown. While the examples shown in FIGS. 3A-3F are representative, they are by no means meant to be exhaustive of the different shapes and configurations that are contemplated by aspects of the present invention. Because of the variation allowed in modern materials, it is contemplated that any shape and configuration of distention structure may be constructed to work in conjunction with aspects of the present invention.

Figure 3A:
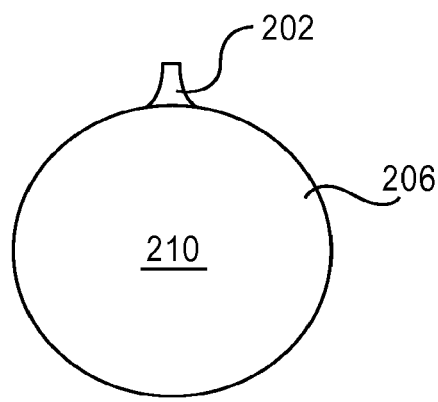
FIGS. 3A-3F show various embodiments of a device constructed in accordance with various aspects of the present invention.

FIG. 3A shows a distention structure 210 with a generally circular perimeter surface 206. The image of FIG. 3A is shown from a top down view. While distention structure 210 is shown with a generally circular perimeter, it is contemplated that the cross section of structure 210 may be one of several shapes. For instance, the cross section may also be generally circular, giving structure 210 an overall generally spherical shape. As another example, the cross section may be rectangular, giving structure 210 a generally tubular shape. Portion 202 is a generally flexible tube that includes one or more functions such as insertion/removal of the structure 210, inflation/deflation, steering of the structure 210 through a body cavity, delivery of fluid or drugs, suction, and/or expansion/contraction of the structure 210.

As such, portion 202 may include one or more internal lumens, actuation mechanisms, such as cables and guide wires, or steering devices.

Figure 3B:
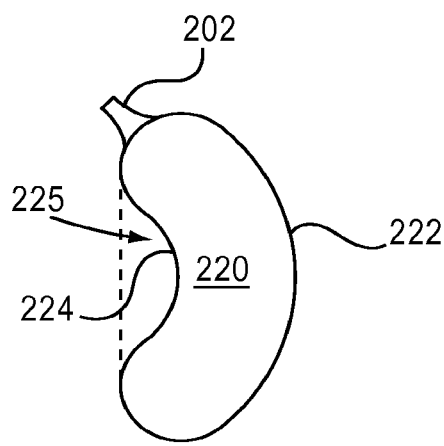

FIG. 3B shows another embodiment of a distention structure 220 that includes a generally kidney shaped perimeter with generally convex surface 222 and generally concave surface 224. Distention structure 220 may be used in situations where distention is indicated in the same general area 225 as where hip joint pathology is located and where treatment is indicated by the surgeon.

Figure 3C:
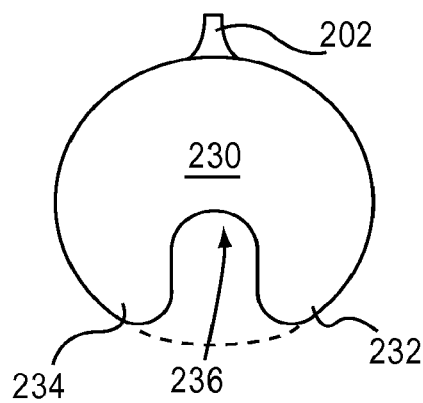

FIG. 3C shows another embodiment of a distention structure 230 that includes a generally horseshoe shaped perimeter with a first lobed portion 234 and a second lobed portion 232 which together define an interior area 236. Distention structure 230 may be used in situations where distention is indicated in the same general area 236 as where hip joint pathology is located and where treatment is indicated by the surgeon.

Figure 3D:
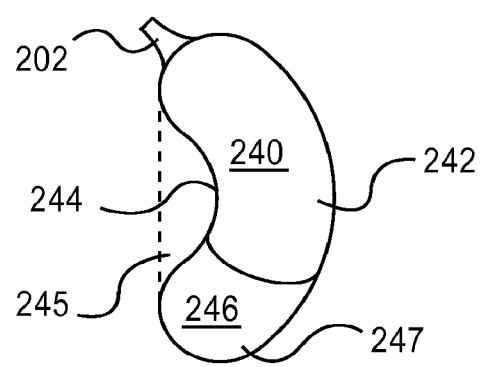

FIG. 3D shows another embodiment of a distention structure 240 that includes a generally kidney shaped perimeter with generally convex surface 242 and generally concave surface 244. Region 246 represents an adjustable area of distention structure 240 that may be deployed in a controllable manner in order to increase or decrease the overall size and area that distention is maintained within the joint capsule. Distention structure 240 may be used in situations where distention and hip joint pathology is indicated proximate the areas 245 and 247.

Figure 3E:
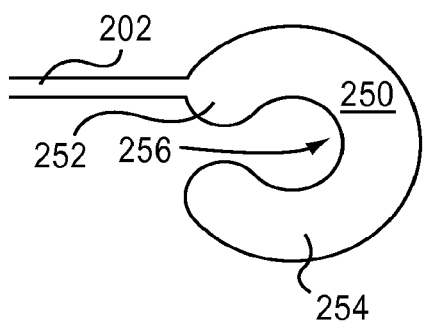
Figure 3F:
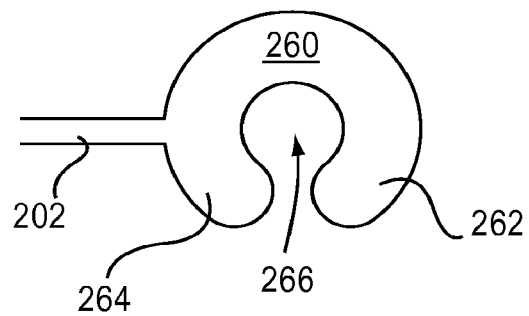

FIGS. 3E and 3F show further embodiments of distention structures 250 and 260 that are generally similar in overall shape to distention structure 230 described above except that portion 202 is coupled to the distention device at different locations in order to change the overall area of treatment that is exposed to a surgeon when the device is deployed. For example in FIG. 3E, portion 202 is coupled to a first lobe 252 of the distention device 250. When deployed, the distention device 250 exposes a region 256 to the surgeon which is in-line with the delivery of portion 202. In FIG. 3F, access and inflation portion 202 is coupled to the proximal edge of distention structure 260 and exposes a region 266 that is somewhat distal with the delivery of portion 202 and intermediate to lobes 264 and 262 of distention device 260.

As mentioned above, the cross sections of the distention devices described above may be one of several shapes such as circular, square, trapezoidal, toroidal, spheroid, oblong, conical, tubular, and/or cylindrical and may therefore define various working space shapes within the hip joint. Benefits of such variety in the shape of the distention devices enable a surgeon to customize the access and visualization he has to the diseased area of the hip joint.

Figure 4A:
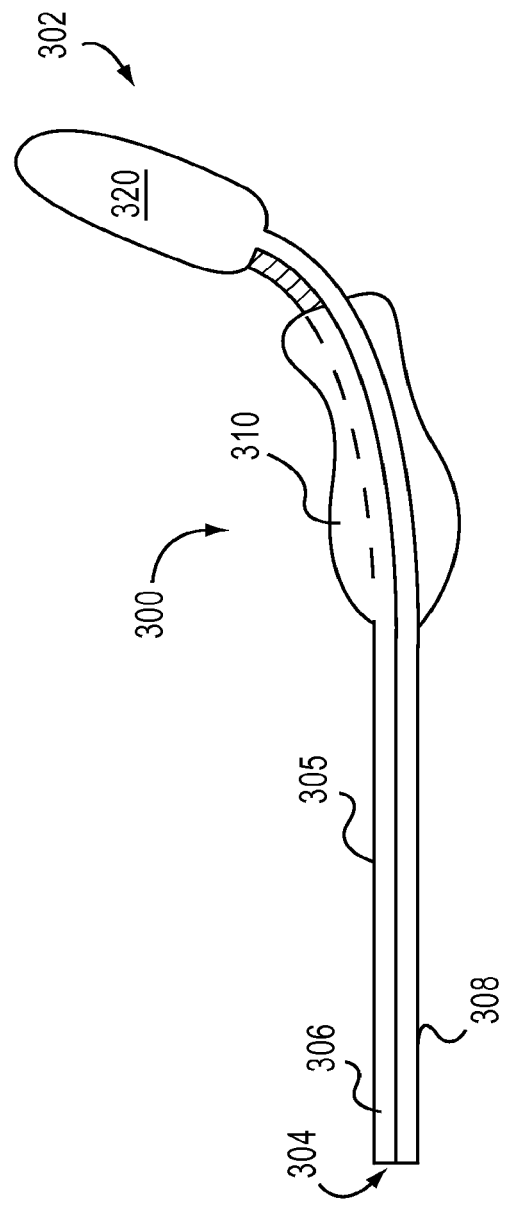
FIGS. 4A and 4B are cross sections of another embodiment of a distention device constructed according to various aspects of the present invention.
Figure 4B:
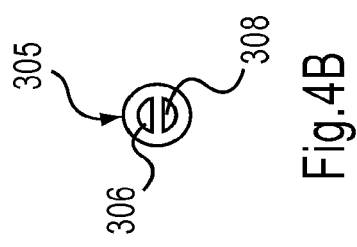

Turning now to FIGS. 4A and 4B, a device 300 is shown that is adapted to deliver one or more distention devices to a location within the anatomy, more particularly, to a location within the hip joint, more particularly to a location between the acetabulum and the femoral head. Device 300 includes a proximal end 304 that is in some embodiments coupled to an actuator or other type of control mechanism adapted to deliver air or fluid to one or more distention devices 310 and 320. In addition, proximal end 304 is preferably coupled to one or more types of control mechanisms that allow a surgeon or other user to advance and otherwise control the location and movement of the device 300. Those of skill in the art will appreciate the extent of the devices that may couple with proximal end 304.

Device 300 is generally tubular in design and includes one or more cannulas adapted to actuate the distention structures 310 and 320. In FIGS. 4A and 4B, two distention structures 310 and 320 are shown, and thus two cannulas 306 and 308 are shown within a sheath 305 of the device 300. Cannula 306 delivers fluid, air or some other actuation material to distention device 310 while cannula 308 delivers fluid, air or some other actuation material to distention device 320. Based on the specific surgical requirements or user preferences, one or more of distention devices 310 and 320 may be actuated in unison or individually. In addition, any number of distention devices and associated tubular lumens may be utilized to provide a wide range of customizable structures and formats to account for varying anatomy and surgical procedures.

In the embodiment of FIGS. 4A and 4B, the distention devices 310 and 320 are depicted as inflatable devices formed from one or more types of surgical quality rubber, silicone or another appropriate flexible material known to those of skill in the art. In some embodiments, the distention devices are formed from a non-elastic material so that the distention force applied by the devices can be controlled and high enough to separate the femoral head from the acetabulum.

Distention devices 310 and 320 are also preferably formed from material able to withstand sufficient pressure in order to apply enough force to the opposing sides of the hip joint to separate them during surgery. In practice, this pressure ranges from about 50 N to about 700 N. Thus, the distention devices 310 and 320 are in some embodiments made from a material that will not expand beyond a certain size. Distention devices 310 and 320 may be sized to take this into account while providing the desired amount of working space within the hip joint.

A problem that arises often in hip surgeries is the ability of the surgeon to gain initial access to the hip joint, and in particular access to the space between the acetabular surface and the femoral head. Ligament and other tissue structures such as the acetabular labrum, capsular ligaments, and other tissue structures serve to keep a very snug fit between the acetabulum and the femoral head. Thus, it is often difficult to initially penetrate this region prior to gaining access to the surgical site within the hip joint itself. Prior art devices and systems do not attempt to deal with this problem in any meaningful way.

Figure 5:
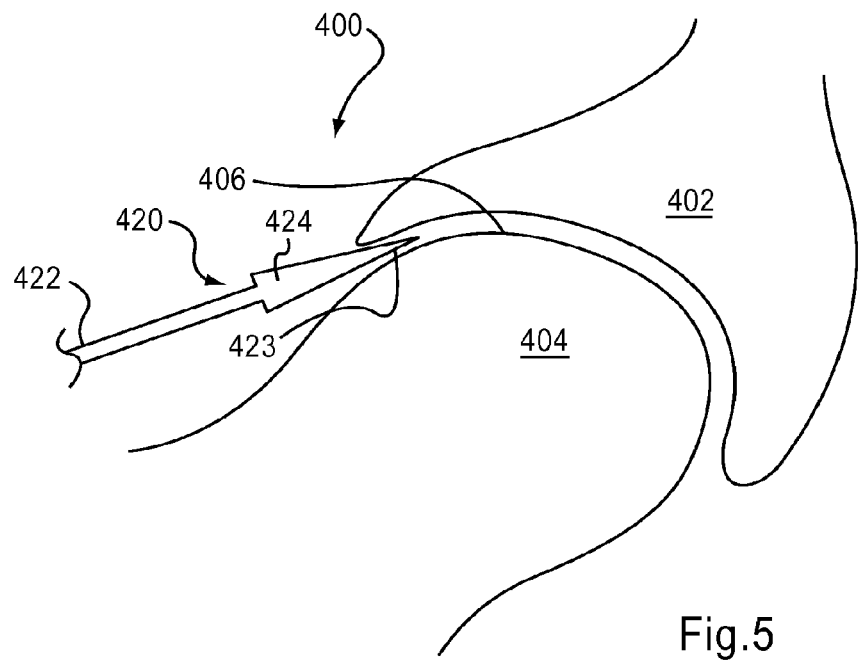
FIG. 5 shows another embodiment of a device constructed in accordance with aspects of the present invention.

FIG. 5 illustrates another aspect of a device constructed in accordance with the present invention designed to address this particular problem. In FIG. 5, the acetabulum 402 and femoral head 404 of a hip joint 400 are initially accessed by a device 420. Device 420 includes a proximal end 422 that projects or extends back to a surgeon or other user and is coupled to a control or other handle device as known in the art. Distal end 423 of device 420 includes structure 424 for penetrating, breaking or otherwise releasing the seal that often exists between acetabulum 402 and femoral head 404. Structure 424, in some embodiments, includes a tapered, wedge or other knife-shaped leading edge in order to aid in displacing the capsular material, acetabular labrum or other tissue that holds the hip joint in place.

Figure 6:
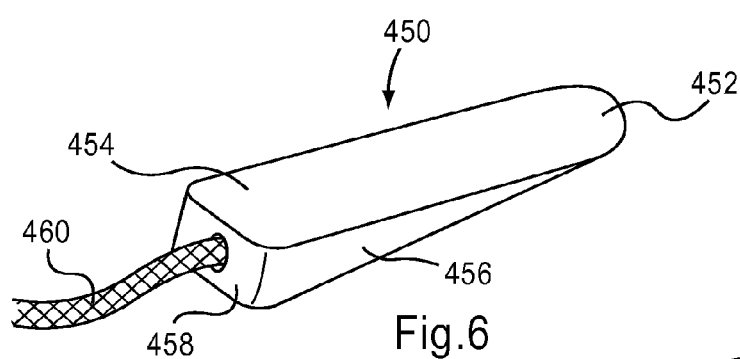
FIGS. 6 and 7 show further embodiments of devices constructed in accordance with aspects of the present invention.
Figure 7:
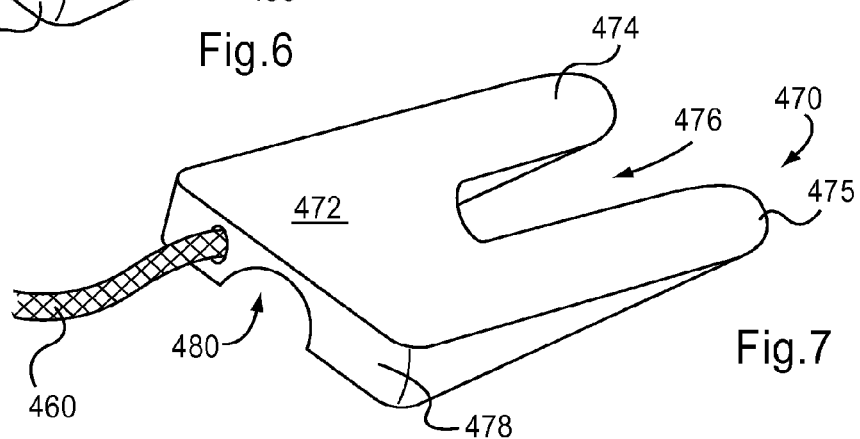

FIGS. 6 and 7 show several alternative embodiments of the device 420 and more particularly the distal structure 424. In FIG. 6, structure 450 includes a tapered and generally knife-shaped leading edge 452 with a generally wedge shaped profile 456. Top surface 454 is preferably smooth to enable a low friction advancement through the structure of the hip joint. In some embodiments, the surface of structure 450 may be coated with an appropriate material or other substance to promote easy entry into the hip joint and acetabular space. Proximal face 458 includes structure for engagement with a cannula or activation structure 460 that allows for the advancement or retraction of the structure 454. Activation structure 460 may be an elongate flexible tube or may be rigid to facilitate the penetration into the acetabular region.

In FIG. 7, structure 470 includes a pair of generally tapered and knife-shaped leading edges 474 and 475 that are similar in format to those in FIG. 6. The structure 470 of FIG. 7 however, includes a mid-line region 476 accessible by a port 480 formed into proximal end 478 of the structure 470. Port 480 allows additional devices to be inserted through structure 470 without needing to remove or maneuver around structure 470. For example, after structure 470 is placed within a hip joint, and has given the surgeon access to the region defined by the intersection of the acetabular surface and the femoral head, a distention device such as those described in conjunction with FIG. 4 above, may be inserted through the port 480 along mid-line region 476 and to the portion of the hip joint that requires distention.

Figure 8A:
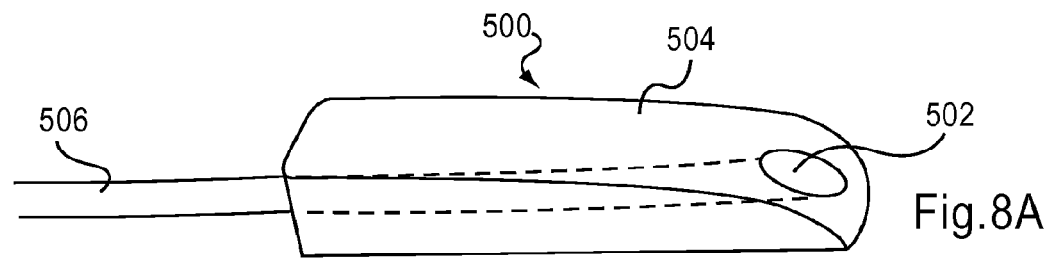
FIGS. 8A and 8B show another embodiment of a device constructed in accordance with aspects of the present invention.
Figure 8B:
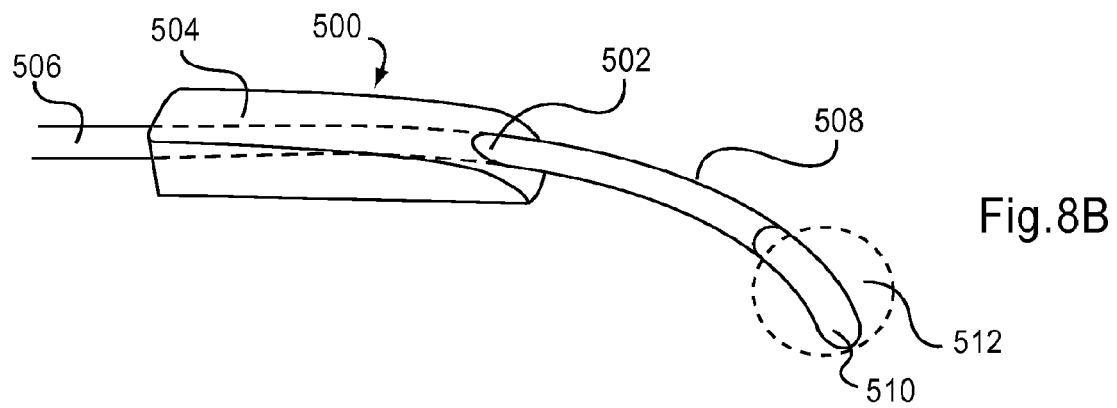

FIGS. 8A and 8B show another embodiment of such a device as it would be used and deployed during a surgical procedure such as a femoral head reconstruction or acetabular labrum repair procedure. A device 500 includes a generally wedge or knife-shaped leading surface 504 and has running through its structure a lumen 502. Catheter 506 is connected with lumen 502 and is adapted to deliver a distention device through the lumen to a region requiring distention and/or surgical treatment. Lumen 502 may also be adapted to deliver a fluid delivery catheter or other pressurized fluid delivery system in order to aid in breaking the seal formed by the hip joint capsule. Distal region 508 of the catheter 506 includes a distal tip 510 that includes one form of distention device 512. In FIG. 8B, distention device 512 is an inflatable or otherwise expandable balloon constructed in a way to distend the acetabular surface away from the femoral head when moved into its expanded position. After deployment, the distention balloon 512 can be deflated and refracted through the lumen 502. As discussed in the embodiments below, device 500 can be removed during a procedure to increase visualization and then re-introduced to remove the distention device 512.

Figure 9A:
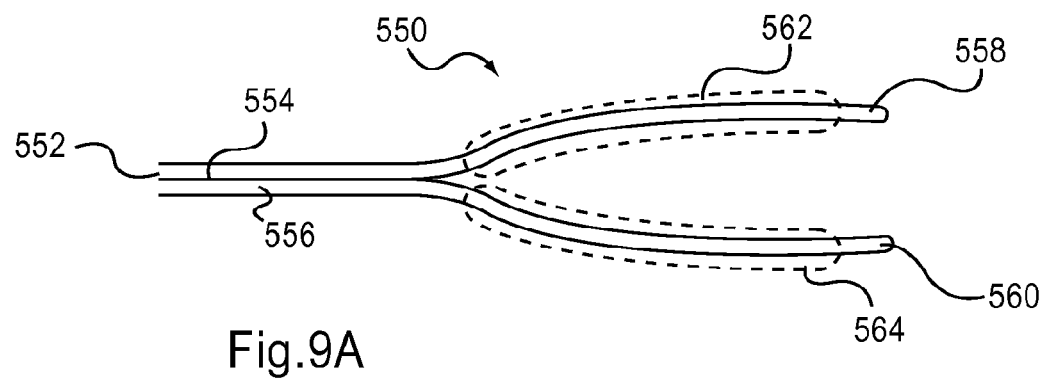
FIGS. 9A and 9B show another embodiment of a device constructed in accordance with aspects of the present invention.
Figure 9B:
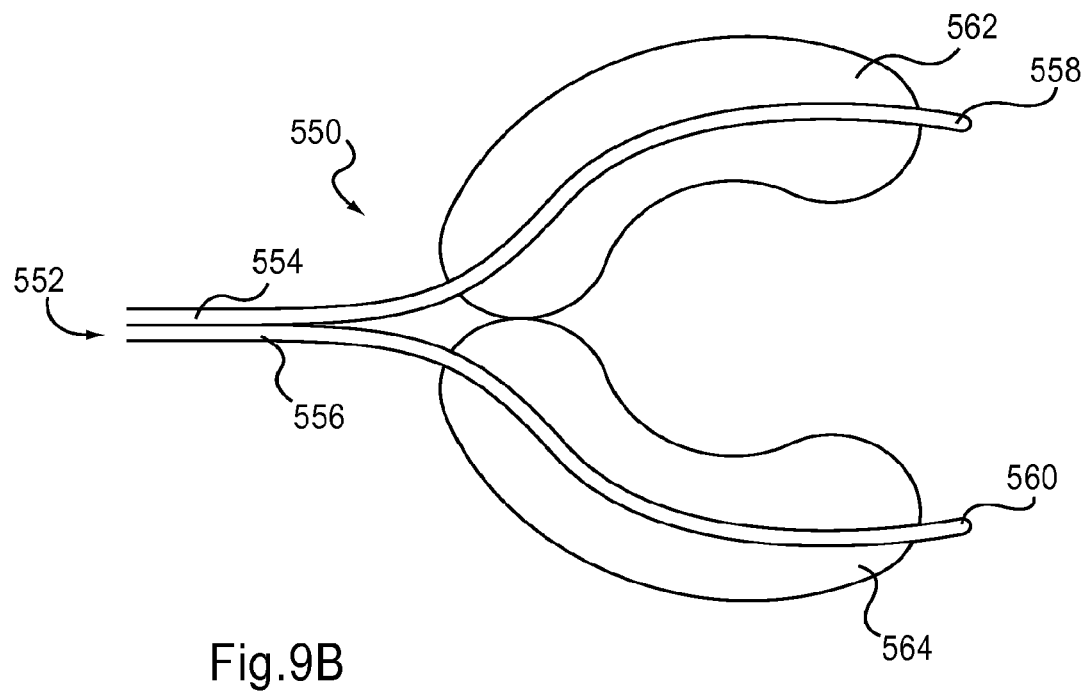

Turning now to FIGS. 9A and 9B, a dual balloon distention device 550 is shown. A proximal end 552 of the device 550 is connected by known means to an actuator or other control mechanism that provides for positional control of the device 550 as well as the ability to provide inflation gas or liquid to each of the distally located inflatable structures 562 and 564. In one embodiment, the distention device 550 is a dual lumen elongate structure with substantially parallel lumens 554 and 556 running along its length. At some medial point along the length of the structure 550, the lumens split into two and create a wishbone shaped device with first distal end 558 and second distal end 560. Inflatable distention portion 562 runs along a portion of the length of lumen 554 and inflatable distention portion 564 runs along another portion of the length of lumen 556. The overall dimension of each of the inflatable portions 562 and 564 may be determined by the procedures involved or the particular anatomy being repaired during operation and it is contemplated that the size, shape and overall orientation of the distention balloon is customizable by the user or surgeon. While it is contemplated that the entire device 550 may be introduced as a whole, each of the lumens 554 and 556 may be independently maneuvered into the anatomy during surgery in order to place them specifically. FIG. 9A shown the inflatable distention portions 562 and 564 in a deflated position, while FIG. 9B shows the inflatable distention portions in a substantially inflated position and in a generally horseshoe-like shape similar to the distention device represented in, e.g. FIG. 3C.

The distention device 550 may be utilized alone or in combination with one of the devices represented in connection with FIGS. 5-8, such that the hip joint is separated and then distended in a single procedure.

While hip pain can be caused by multiple pathologies, FemoroAcetabular Impingement (FAI) and injuries to the acetabular labrum are the most common pathologic findings identified at the time of hip arthroscopy. FAI can cause labral injury and early osteoarthritis. Causes of labral tears include trauma, FAI, capsular laxity, dysplasia, and degeneration. Various surgical techniques have been used to restore function of the hip joint and labrum. Suture anchor repair is one preferred and well-known method of labrum repair. The goal of arthroscopic treatment of a torn labrum and FAI is to relieve pain by eliminating the unstable flap tear and bony morphology that causes hip discomfort. The goals of these treatments are to maintain the function of the hip joint and decrease the development of premature osteoarthritis. Aspects of devices and methods in accordance with the present invention are useful in combination with these surgical labrum repair techniques.

Figure 10:
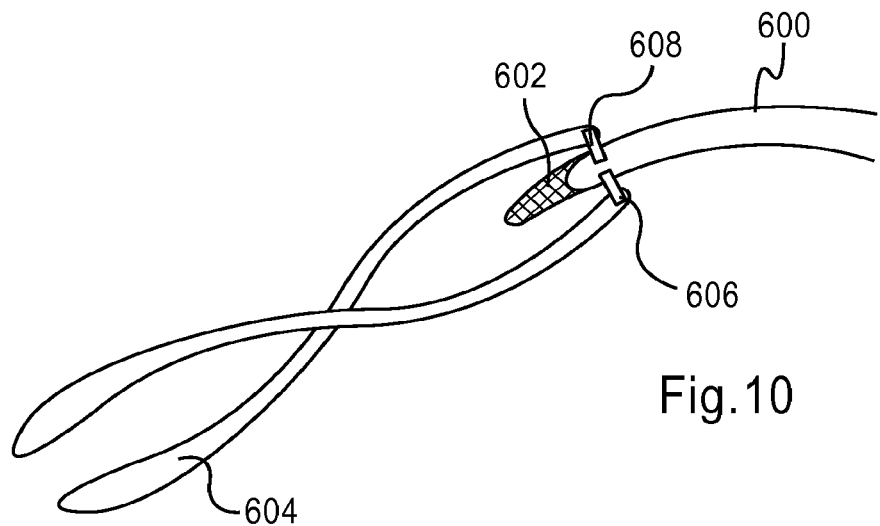
FIGS. 10 and 11 show one of the general techniques used to repair and/or reconstruct the acetabular labrum.
Figure 11:
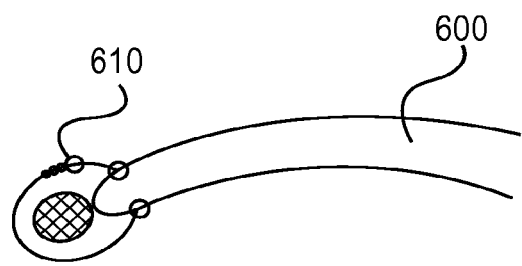

As an example of a surgical technique that would benefit from the use of devices and methods disclosed herein, FIGS. 10 and 11 illustrate a generalized view of the portion of the acetabular labrum that may become detached and in need of repair. These figures also illustrate in general terms, the process for repairing the labrum through a known suture anchor technique. As mentioned above, the acetabular labrum 602 is a ring of cartilage that surrounds the socket of the hip joint 600 (i.e. the acetabulum). When the acetabular labrum 602 becomes detached from the boney portion of the acetabulum 600, repair or reconstruction is needed. As shown in FIGS. 10 and 11, one known method of repair involves providing at least a pair of anchors 606 and 608 via a surgical tool 604 and then using sutures 610 to reattach the labrum 602 to the bone 600.

Figure 12A:
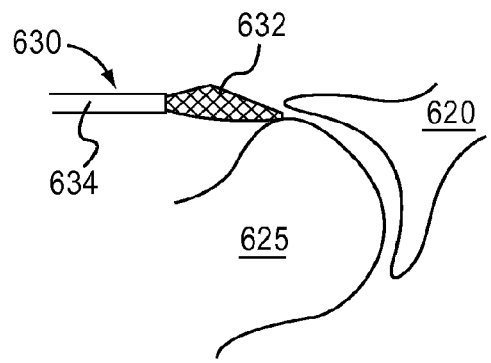
FIG. 12A-12F illustrate one method of using a device constructed in accordance with aspects of the present invention.
Figure 12B:
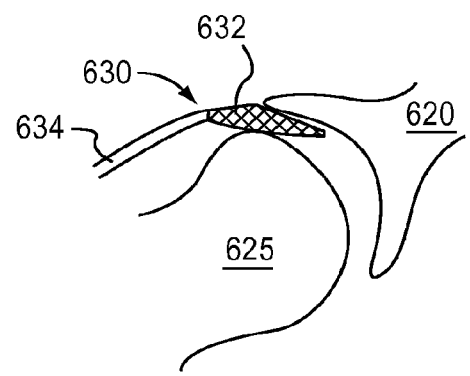
Figure 12C:
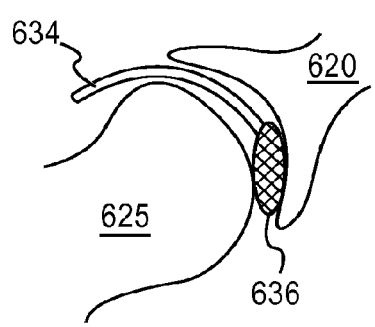
Figure 12D:
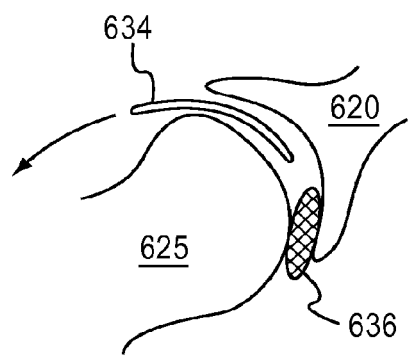
Figure 12E:
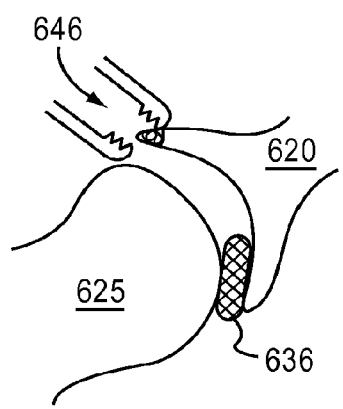
Figure 12F:
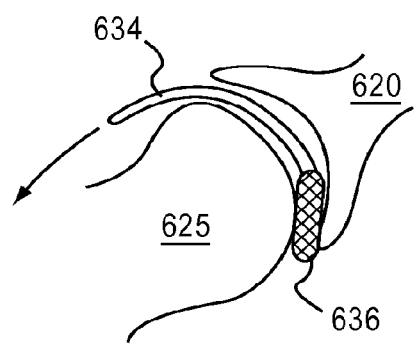

Repair of the acetabular labrum, or some other hip repair or reconstruction surgery such as FAI decompression, removal of loose bodies, labral debridement, microfracture chondroplasty, osteoplasty, total hip replacement, hip resurfacing, tendon release, etc. either as done in the past or as disclosed herein, may be accomplished in combination with one or more of the distention devices and/or techniques described herein. FIGS. 12A-12F illustrate one embodiment of a device constructed in accordance with aspects of the present invention used in connection with an acetabular labrum repair. Referring to FIGS. 12A-12F, Acetabulum 620 and femoral head 625 are initially distended or distracted via a surgical tool 630. In general terms, tool 630 includes an elongate member 634 that directs and/or actuates distal end 632. Distal end 632 may be formatted and designed according to any of the embodiments disclosed herein. For example, distal end may incorporate an inflatable distention structure and/or an acetabular distracting structure such as the wedge shaped embodiment disclosed in conjunction with FIGS. 5-8. In either case, the distal end 632 advances through the space between the acetabulum 620 and the femoral head to a point where distention of the hip joint is desired, such as depicted in FIG. 12C. In one embodiment, distal end 632 is advanced by pushing or otherwise manually manipulating the distal end through the hip joint. Once located within the hip joint, a distention device is activated, e.g. inflated, to a point where appropriate distention is accomplished. In the example of FIG. 12C, a balloon 636 or other inflatable portion is positioned and elongate member 634 is removed from the distended hip joint. At this point, repair to the acetabular labrum can be accomplished through any technique known or as disclosed herein such as depicted at 646. For treatment of FAI, once the impinging lesion has been visualized, a long motorized burr may be introduced in to the working space to perform an osteoplasty to resect any impinging bone. A 'rim trimming' procedure may also be performed in which the labrum is detached, the rim of the acetabulum is resected with a motorized burr, and the labrum reattached with anchors. If the labrum is too badly damaged for repair, a labral reconstruction procedure may be performed. In this procedure, a graft of tissue from the Iliopsoas or Iliotibial tendon or other appropriate tissue is used to reconstruct the labrum with the use of suture and bone anchors.

Turning now to FIG. 13, one embodiment of a device 700 adapted to gain access to the space between the acetabulum and femoral head and/or distend the hip joint is shown. The device 700 generally includes a handle assembly 702 and a trigger or other actuation structure 704 as many known arthroscopic surgical instrument include. An elongate tubular structure 710 includes a proximal end 711 and a distal end 712. A portion 706 of the proximal end 711 allows rotation of the entire elongate member 710. Tactile grip portion 708 provides improved mobility and maneuverability of the elongate member 710 to a user. The distal end 712 of the elongate member includes a wedge shaped structure with opposing jaw portions 714 and 716. The elongate structure 710 includes at least one lumen through which a tubular distention device 750 may extend through. At a distal end of the distention device 750 is a distention balloon or other distention structure 760. In the embodiment of FIG. 13, the distention structure 760 is shown as an inflatable balloon in its generally collapsed position. As depicted by the arrows in FIG. 13, both the elongate member 710 of the device 700 as well as the tubular distention device 750 may be rotatable such that the distal end 712 and the distention structure 760 may be aligned in any position relative to the hip joint as a whole, the acetabulum, the femoral head or any of the other structures within the hip joint anatomy. As an alternative, the entire device 700 may be rotated in order to specifically position the distention structure 760 or the distal end 712.

Figure 14:
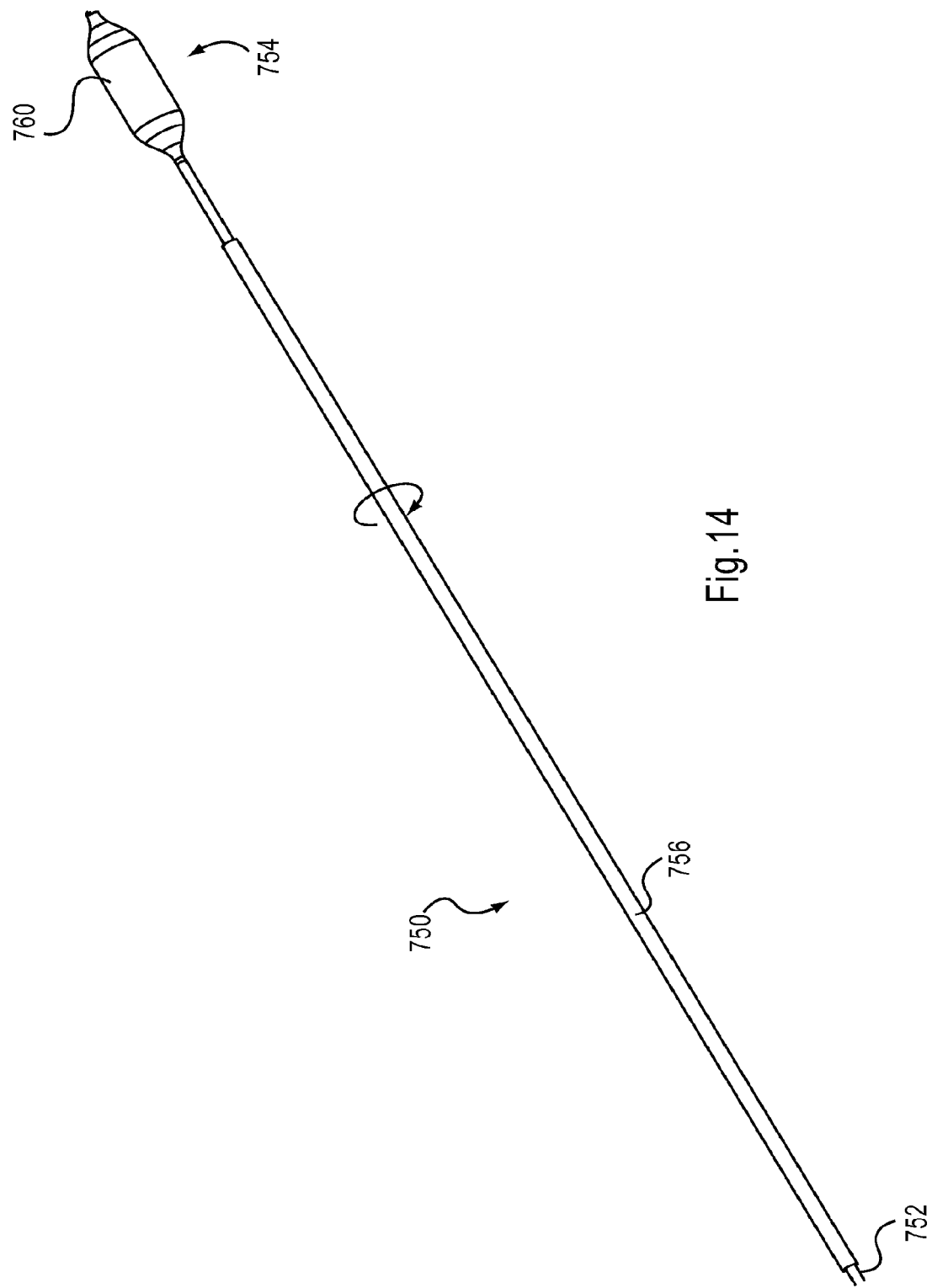
FIG. 14 is another embodiment of a surgical tool constructed in accordance with aspects of the present invention.

FIG. 14 shows an isolated view of the overall distention device 750 including a proximal end 752 which in one embodiment is coupled with an actuation device such as a compressed air or hydraulic pump system that acts to inflate or otherwise expand the distention structure 760 located at the distal end of the distention device 750. A flexible tube or other elongate member 756 provides the ability to extend or otherwise position the distention structure 760 at any desired point within the hip joint. Distention device 750 may be rotated by a user so that the orientation of distention structure 760 may be moved dynamically by a user.

Figure 15:
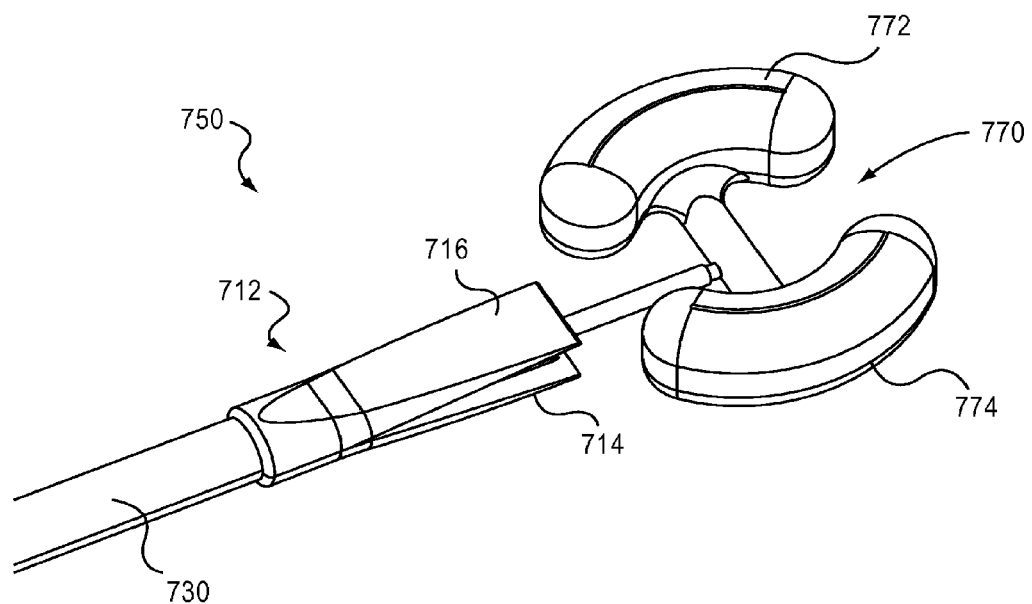
FIG. 15 is a further embodiment of a surgical tool constructed in accordance with aspects of the present invention.

FIG. 15 shows an alternate embodiment of a distention structure 770 that includes a pair of distention lobes 772 and 774. As described previously, the shape, size, number, and orientation of the distention structure may be modified according to the particular procedure and/or anatomy being operated on. In any case, the distention structure is capable of being collapsed within a sheath or other containment structure so that it may be deployed through the tool 750.

Figure 16:
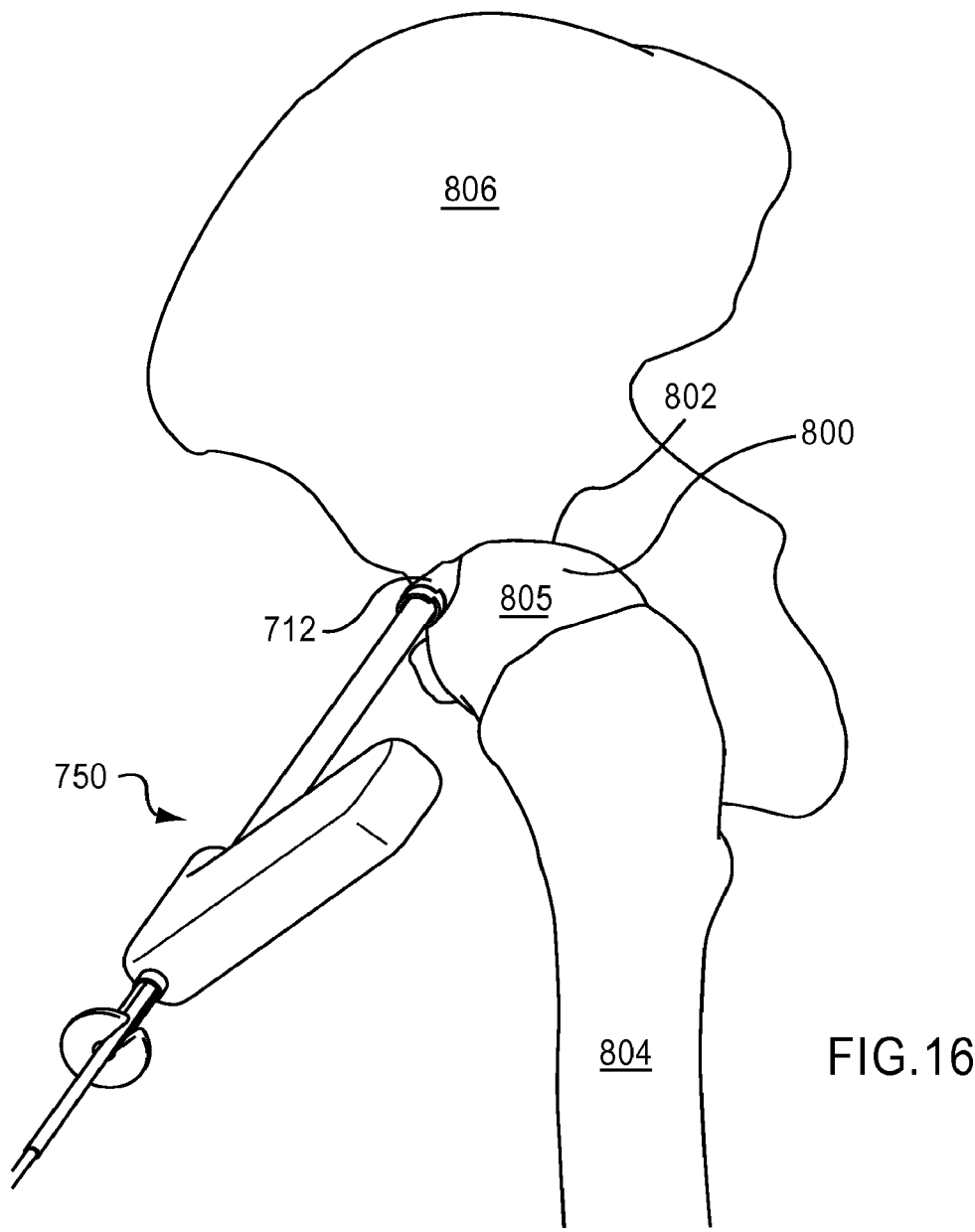
FIG. 16 is a general representation of a hip joint and how devices constructed in accordance with aspects of the present invention may be utilized.

FIG. 16 shows a general representation of a hip joint 800 including pelvis 806, acetabular surface 802, femoral head 805 and femur 804. In use, the device 750 utilizes the wedge shaped distal structure 712 to first break the seal between the acetabulum and femoral head. After this seal is broken, distention and/or repair to the anatomy can take place as described above.

One or more distention structures may be used in connection with devices and methods in accordance with aspects of the present invention. For example, a first balloon might be placed near the Ligamentum Teres Femoris (the ligament near the head of the femur). A second, possibly smaller distention structure is placed superior to the first in order to move the head of the femur inferiorly. Alternatively, a single distention structure with multiple expandable chambers may also be utilized. The shape of the chambers are preferably configured to the specific anatomy as is shown in the attached figures and drawings. In some embodiments the distention structures are inflatable and/or expandable balloons.

These balloons and/or chambers are then inflated (e.g. with saline or air) in various configurations to position the head of the femur relative to the Acetabulum in order to achieve the required and/or desired surgical access. In still other embodiments, a third balloon could be placed near the neck of the femur to create further working space by distending the ligaments and joint capsule. This could also be a single chamber of a multi-chamber balloon versus a completely separate balloon. This balloon could be combined with an endoscope for visualization.

In accordance with other aspects, devices and methods are disclosed that utilize balloons, or other atraumatic means and/or devices, to distend soft tissues surrounding the femur away from the bony structure in order to create a working space for a variety of endoscopic hip surgeries, many of which were described previously. Because current methods pump fluid directly into the joint in order to move these tissues, and because the capsule is cut during the surgical procedure, it can not hold the fluid pressure. It therefore collapses and interferes with visualization and the surgical instruments. Currently there is no effective means of moving these tissues to gain better access and working space. Embodiments of the present invention allow easier access and visualization to the proximal femur during arthroscopic hip surgery.

During many endoscopic hip procedures, the joint capsule and other soft tissue structures occasionally get in the way of the endoscope and other instruments, obstructing the visual and working field. In accordance with aspects of the present invention, a balloon, or other structure, is placed partially around the femoral neck at the distal attachment of the joint capsule, near the 'zona orbicularis', to act as a tent or other enclosure to keep loose tissue free from the working area.

In one embodiment, the device consist of three main elements:

1) A space creating element (in some embodiments this is a balloon or other inflatable or expandable structure). This structure could be made of various materials, including polyurethane, Nylon, PVC, and other compliant or non-compliant materials.

2) A delivery tool used to deliver the balloon into position, release the balloon, and possibly to remove it or re-position it as required.

3) An inflation device. This could be a standard syringe, or an off the shelf inflator that is used for angioplasty, or a specially made device. The inflation device could also be incorporated into the delivery tool or similar to the distention balloon described above.

One embodiment of a procedure performed in accordance with these aspects is as follows:

1. Establish an anterolateral and mid-lateral portal into the joint capsule using an appropriate surgical technique.
2. Introduce the delivery tool into the joint capsule
3. Insert a balloon into position with the delivery tool.
4. Remove the delivery tool.
5. Inflate the balloon with sterile saline via an inflation device.
6. Re-position the balloon if necessary.
7. Surgical procedure is performed as required (balloon may be deflated and re-inflated, re-positioned, or even removed during the procedure. The delivery tool may be used to accomplish these actions, or standard surgical tools may be used.
8. Deflate the access system, either with the inflation device, or manually punctured (e.g. scalpel, beaver blade)
9. Remove balloon, either with the Delivery tool or manually (e.g. forceps).
10. Complete procedure per standard of care (capsule closed, etc.).

The outer surface of the balloon may in some embodiments be covered with friction creating material. The entire surface of the balloon can be covered or only certain areas as appropriate. For example, a friction material (e.g. rough hook side of Velcro) on the upper surface to hold against soft tissue, while keeping the bottom surface smooth for contact to the bone and vascular structures located on the bone surface. Alternatively, the balloon material may be formed from two layers of polyurethane sheet with a layer of nylon mesh (filter material) in between. The sheets may be laminated together, held by an RF Weld around the edge or bound together by any other known or contemplated technique.

Figure 17:
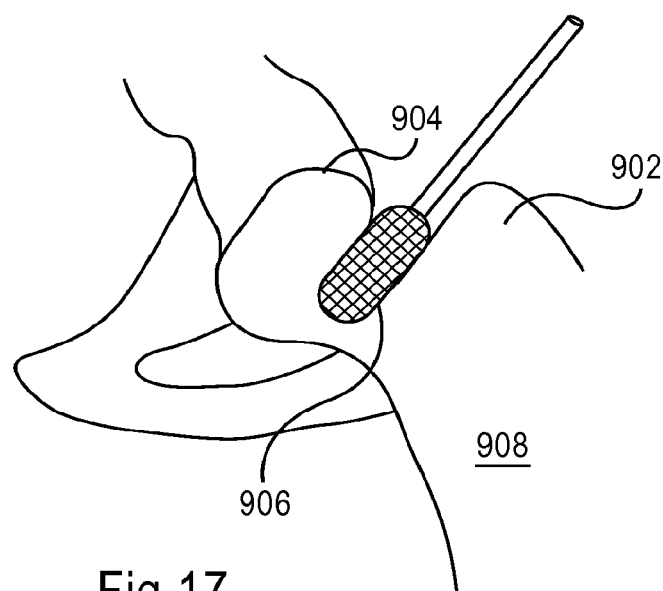
FIG. 17 is another embodiment of a device constructed in accordance with aspects of the present invention.
Figure 18:
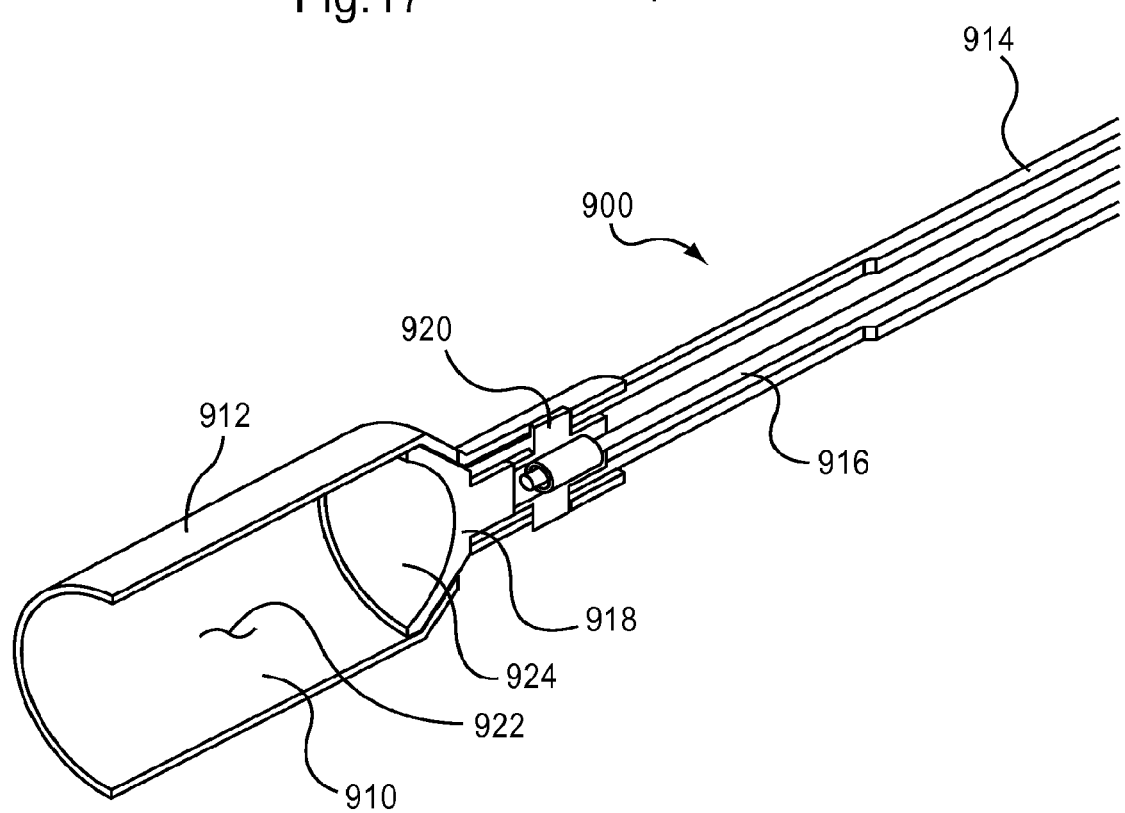
FIGS. 18 and 19 are further embodiments of a device constructed in accordance with aspects of the present invention.
Figure 19:
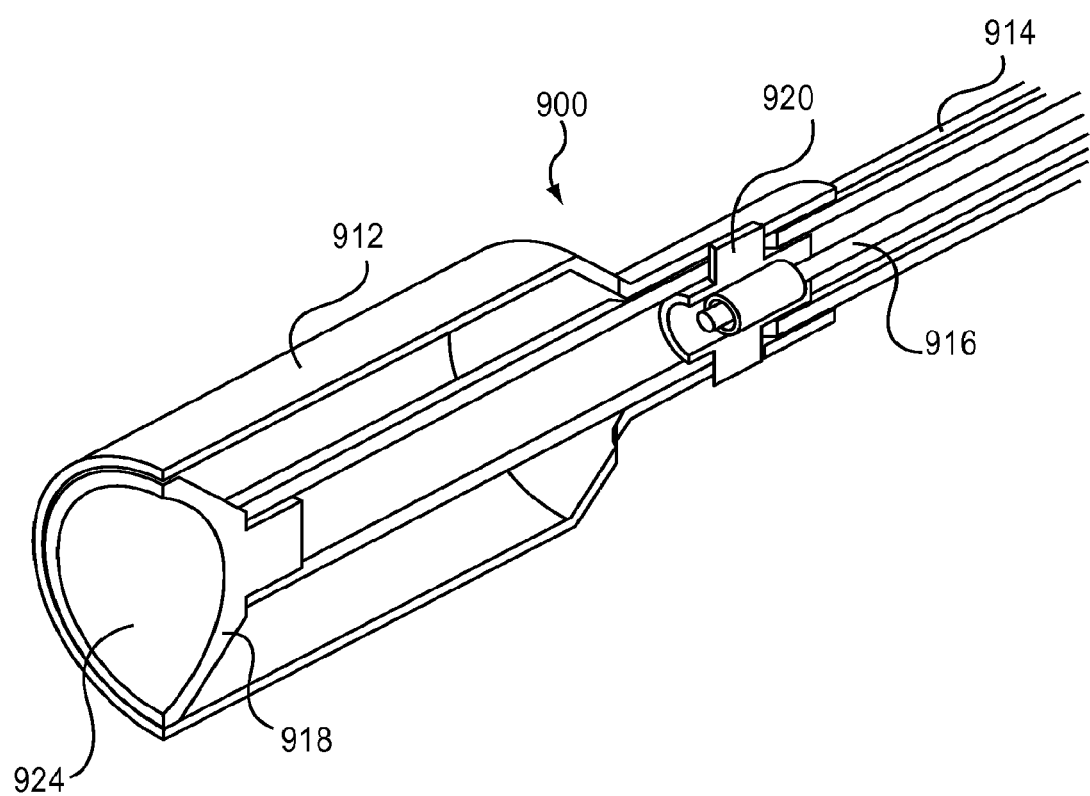

FIGS. 17-19 describe one embodiment of a delivery tool adapted to position a distention or access device as described above. FIG. 17 shows the general anatomy of the hip, including femur 908 and femoral head 904 and how an access device 906 may be positioned proximate to the femoral neck and adjacent greater trochanter 902 and in the area of zona orbicularis in order to move tissue from the field of view or surgical site.

FIG. 18 illustrates one embodiment of a delivery device 900 that includes a main shaft 914 enclosing a cable 916, a plunger 918 and a cylinder 910. The cylinder 910 defines a cavity 922 that is adapted to carry a collapsed distention balloon or other distention structure. A shuttle 920 couples with the plunger 918 and when retracted by the cable 916 deploys the distention device carried in the cavity 922 when located at the desired point within the anatomy.

FIG. 18 shows the device 900 in its retracted position while FIG. 19 show the device in its deployed position, with cylinder 910 pulled back moving plunger 918 forward and releasing the distention device from the cavity 922

Those skilled in the art can readily recognize that numerous variations and substitutions may be made in the invention, its use and its configuration to achieve substantially the same results as achieved by the embodiments described herein. Accordingly, there is no intention to limit the invention to the disclosed exemplary forms. Many variations, modifications and alternative constructions fall within the scope and spirit of the disclosed invention.

What is claimed is:

1. A medical instrument for distending a joint, the joint including a first joint surface and a second joint surface, the medical instrument comprising:

a tubular member having a proximal end and a distal end;

a lumen extending through the tubular member between the proximal and distal ends of the tubular member; a distal opening of the lumen at the distal end the tubular member;

a proximal opening of the lumen at the proximal end of the tubular member;

at least one expandable unit in fluid communication with the distal opening such that the distal opening of the lumen fluidly communicates with the interior of the at least one expandable unit;

a tapered distal structure extending from the distal end of the tubular member, the tapered distal structure configured for penetrating capsular tissue;

a fluid movement device attachable to the proximal end of the lumen capable of establishing a fluid connection between the fluid movement device and the proximal opening of the lumen, and capable of establishing a fluid connection between the fluid movement device and the interior of the at least one expandable unit by fluid flow through the lumen and into the interior of the at least one expandable unit; and a handle attachable to the tubular member.

2. The medical instrument of claim 1, wherein the first joint surface is acetabulum and the second joint surface is a femoral head.

3. The medical instrument of claim 1, further comprising: an at least second lumen of the tubular member.

4. The medical instrument of claim 3, wherein the at least second lumen has a first opening at or near the proximal end of the tubular member and is a blind lumen, the at least second lumen capable of receiving a guide wire.

5. The medical instrument of claim 4, wherein the first opening of the at least second lumen is separate from the opening of the tubular member extending between the proximal and distal ends of the tubular member.

6. The medical instrument of claim 1, wherein the at least one expandable unit fluidly attachable to the distal end of the tubular member is positionable within a body site by maneuvering of the handle.

7. The medical instrument of claim 6, wherein the body site is a joint.

8. A method of distending a joint, the joint including a first joint surface and a second joint surface, comprising: using a medical instrument according to claim 1.

9. The method of claim 8, wherein the distal end of the tubular member is advanced into a desired location in a joint to be distended; and the at least one expandable unit is expanded by fluid pressure from the fluid movement device through the lumen of the tubular member, thereby distending within the joint.

10. The method of claim 9, further comprising maneuvering the at least one expandable unit into a desired position in the joint before, during, or after expansion.

11. The method of claim 9, further comprising maneuvering the at least one expandable unit into a desired position in the joint before, during or after expansion by a guide wire located within at least a second lumen of the tubular member having a first opening at or near the proximal end of the tubular member, and wherein the at least second lumen is a blind lumen.

12. The method of claim 9, further comprising guiding by maneuvering of the handle the at least one expandable unit into a desired position in the joint before, during or after expansion in a joint.

13. A medical device for distending a joint, the joint including a first joint surface and a second joint surface, the medical device comprising:

a tubular member having a proximal end and a distal end;

a lumen extending through the tubular member between the proximal and distal ends of the tubular member; a distal opening of the lumen at the distal end the tubular member;

a proximal opening of the lumen at the proximal end of the tubular member;

at least one expandable unit in fluid communication with the distal opening such that the distal opening of the lumen fluidly communicates with the interior of the at least one expandable unit;

a tapered distal structure extending from the distal end of the tubular member, the tapered distal structure configured for penetrating capsular tissue; and a fluid delivery system attachable to the proximal end of the lumen, capable of establishing a fluid connection between the fluid delivery system and the proximal opening of the lumen, and capable of establishing a fluid connection between the fluid delivery system and the interior of the at least one expandable unit by fluid communication between them through the lumen.

14. The medical device of claim 13, further comprising a handle attachable to the tubular member.

15. The medical device of claim 14, further comprising:
an at least second lumen of the tubular member wherein the at least second lumen has a first opening at or near the proximal end of the tubular member, is a blind lumen ending within a distal region of the tubular member, and is capable of receiving a guide wire.

16. The medical device of claim 15, wherein the at least one expandable unit fluidly attachable to the distal end of the tubular member is positionable within a body site by maneuvering of the handle.

* * * * *